(12) United States Patent
Zhu et al.

(10) Patent No.: US 11,517,541 B2
(45) Date of Patent: Dec. 6, 2022

(54) APPLICATIONS OF SPERMIDINE AND ITS DERIVATIVES

(71) Applicant: GENEHEAL BIOTECHNOLOGY CO., LTD., Guangdong (CN)

(72) Inventors: Wei Zhu, Guangdong (CN); Wuguang Pan, Guangdong (CN)

(73) Assignee: Geneheal Biotechnology Co., Ltd., Guangzhou (CN)

( * ) Notice: Subject to any disclaimer, the term of this patent is extended or adjusted under 35 U.S.C. 154(b) by 145 days.

(21) Appl. No.: 16/606,655

(22) PCT Filed: Mar. 12, 2018

(86) PCT No.: PCT/CN2018/078723
§ 371 (c)(1),
(2) Date: Oct. 18, 2019

(87) PCT Pub. No.: WO2018/192323
PCT Pub. Date: Oct. 25, 2018

(65) Prior Publication Data
US 2020/0330403 A1    Oct. 22, 2020

(30) Foreign Application Priority Data
Apr. 20, 2017 (CN) .......................... 201710262440.8

(51) Int. Cl.
A61K 31/132 (2006.01)
(52) U.S. Cl.
CPC .................................. A61K 31/132 (2013.01)
(58) Field of Classification Search
CPC .................................................. A61K 31/132
See application file for complete search history.

(56) References Cited

U.S. PATENT DOCUMENTS

| | | | |
|---|---|---|---|
| 3,462,529 | A | 8/1969 | Forget et al. |
| 4,952,585 | A | 8/1990 | Sunkara et al. |
| 5,541,230 | A | 7/1996 | Basu et al. |
| 6,235,794 | B1 | 5/2001 | Bergeron, Jr. |
| 6,660,719 | B2 | 12/2003 | Bantia |
| 7,056,945 | B1 | 6/2006 | Poulos et al. |
| 7,122,190 | B2 | 10/2006 | Bolognesi |
| 8,229,673 | B2 | 7/2012 | Palsson |
| 8,949,032 | B2 | 2/2015 | Famili |
| 10,197,574 | B2 | 2/2019 | Stroitgin |
| 2003/0022209 | A1 | 1/2003 | Freidman |
| 2003/0082511 | A1 | 5/2003 | Brown |
| 2004/0029149 | A1 | 2/2004 | Palsson |
| 2004/0052820 | A1 | 3/2004 | Bolognesi |
| 2006/0147899 | A1 | 7/2006 | Famili |
| 2008/0176907 | A1 | 7/2008 | Silverman |
| 2009/0030005 | A1 | 1/2009 | Kamb |
| 2014/0127820 | A1 | 5/2014 | Strongin |
| 2014/0141010 | A1 | 5/2014 | Oommen |
| 2015/0302141 | A1 | 10/2015 | Famili |
| 2016/0223558 | A1 | 8/2016 | Strongin |
| 2016/0369281 | A1 | 12/2016 | He |
| 2019/0209493 | A1 | 7/2019 | Pan |
| 2019/0209499 | A1 | 7/2019 | Pan |
| 2019/0298722 | A1 | 10/2019 | Ceballos-Piot |

FOREIGN PATENT DOCUMENTS

| | | | |
|---|---|---|---|
| CN | 101037423 A | 9/2007 | |
| CN | 101189002 | 5/2008 | |
| CN | 103748091 | 4/2014 | |
| CN | 104918611 A | 9/2015 | |
| CN | 105246509 A | 1/2016 | |
| CN | 106399380 A | 2/2017 | |
| EP | 0116693 | 8/1984 | |
| EP | 0116693 B1 * | 6/1987 | ............. A61P 43/00 |
| EP | 0270349 | 6/1988 | |
| EP | 3613416 | 2/2020 | |
| JP | 2001-172244 | 6/2001 | |
| WO | WO 1990/01036 | 2/1990 | |
| WO | WO 1997/011691 | 4/1997 | |
| WO | WO 1999/051213 | 10/1999 | |
| WO | WO 2003/037371 | 5/2003 | |
| WO | WO 2003/062255 | 7/2003 | |
| WO | WO 2005/013932 | 2/2005 | |
| WO | WO 2005/020885 | 3/2005 | |
| WO | WO 2006/099095 | 9/2006 | |
| WO | WO 2013/045826 | 4/2013 | |
| WO | WO 2014/067038 | 5/2014 | |
| WO | WO 2014/075187 | 5/2014 | |
| WO | WO 2014/117272 | 8/2014 | |
| WO | WO 2018/059211 | 4/2018 | |
| WO | WO 2018/059212 | 4/2018 | |
| WO | WO 2018/059395 | 4/2018 | |
| WO | WO 2018/059396 | 4/2018 | |
| WO | WO 2018/192323 | 10/2018 | |

OTHER PUBLICATIONS

Zips et al., In vivo, 2005, 19, 1-8.*
Sikora, Current Science 2001, 81(5), 549-554.*
Schmutzler et al. European Journal of Endocrinology 2000, 143, 15-24.*
Invasive Mammary Carcinoma (IMC), available on Jun. 21, 2021 at https://www.hopkinsmedicine.org/breast_center/breast_cancers_other_conditions/invasive_mammary_carcinoma.html.*
Zhao et a., The purinosome, a multi-protein complex involved in the de novo biosynthesis of purines in humans, Chem. Commun., 2013, 49, 4444.*
Zhang, Study on Mechanism of Apoptosis Induced by Spermine in Human Cervical Cancer HeLa Cells, China Master's Thesis Full-text database, Apr. 1, 2013.*
McCloskey et al., Polyamine Analogue Induction of Programmed Cell Death in Human Lung Tumor Cells, Clinical Cancer Research, vol. 2., 441-446, Mar. 1996.*

(Continued)

*Primary Examiner* — Svetlana M Ivanova
(74) *Attorney, Agent, or Firm* — Fish & Richardson P.C.

(57) ABSTRACT

Disclosed are applications of spermidine or its pharmaceutically acceptable derivatives. The inventors performed calculation and analysis using software based on existing data relating to protein and small-molecule structures, and screened out compounds which can effectively interfere with the activity of PAWS and thus reduce SAICAR synthesis, thereby achieving the goal of treating or improving tumors. It is expected to produce better effect in the treatment or improvement of tumors.

20 Claims, 4 Drawing Sheets

(56) References Cited

OTHER PUBLICATIONS

Hahm, The Effect of Protein Kinase C Modulation with Bryostatin 1 on Paclitaxel-Induced Growth Inhibition and Apoptosis in Human Breast Cancer, Award No. DAMD17-97-1-7338, Report date: Jan. 2000, available at https://apps.dtic.mil/sti/pdfs/ADA390788.pdf.*
Cellosaurus MDA-MB-468 (CVCL_0419), entry creation—Apr. 4, 2012, available at https://web.expasy.org/cellosaurus/CVCL_0419.*
Ha et al., Structural Specificity of Polyamines and Polyamine Analogues in the Protection of DNA from Strand Breaks Induced by Reactive Oxygen Species, Biochemical and Biophysical Research Communications 244, 298-303 (1998).*
Casero et al., Recent Advances in the Development of Polyamine Analogues as Antitumor Agents, J. Med. Chem. 2009, 52, 4551-4573.*
Seiler, Pharmacological aspects of cytotoxic polyamine analogs and derivatives for cancer therapy, Pharmacology & Therapeutics 107 (2005) 99-119.*
Igarashi et al., Spermine-like functions of N1, N12-bis(ethyl)spermine: stimulation of protein synthesis and cell growth and inhibition of gastric ulceration, Biochem Biophys Res Commun, Oct. 30, 1990;172(2):715-20.*
Medlineplus.gov, [online], "Adenylosuccinate Lyase Deficiency," Aug. 18, 2020, retrieved on Dec. 18, 2020, retrieved from URL <https://medlineplus.gov/download/genetics/condition/adenylosaccinate-lyase-deficiency.pdf>, 4 pages.
Mouchegh et al., "Lethal fetal and early neonatal presentation of adenylosuccinate lyase deficiency: observation of 6 patients in 4 families," J. Pediatr,. 2007, 150(1):57-61.
Perez-Duenas et al., "Novel features in the evolution of adenylosuccinate lyase deficiency," Eur. J. Pedi. Neurol, 2012, 16(4):343-348.
Hanahan, D.and R.A. Weinberg, "Hallmarks of cancer: the next generation". Cell, 2011.144(5): p. 646-74.
Hsu, P.P. and D.M. Sabatini, Cancer cell metabolism: Warburg and beyond. Cell, 2008.134(5): p. 703-7.
Christofk, H.R., et al., *The M2 splice isoform of pyruvate kinase is important for cancer metabolism and tumour growth*. Nature, 2008.452(7184): p. 230-3.
Wolf, A., et al., *Hexokinase 2 is a key mediator of aerobic glycolysis and promotes tumor growth in human glioblastoma multiforme*. J Exp Med, 2011.208(2): p. 313-26.
Chen, J., et al., *Shikonin and its analogs inhibit cancer cell glycolysis by targeting tumor pyruvate kinase-M2*. Oncogene, 2011. 30(42): p. 4297-306.
Anastasiou, D., et al., *Pyruvate kinase M2 activators promote tetramer formation and suppress tumorigenesis*. Nat Chem Biol, 2012.8(10): p. 839-47.
Vander Heiden, M.G., *Exploiting tumor metabolism: challenges for clinical translation*. J Clin Invest, 2013.123(9): p. 3648-51.
Ciardo, F., C.Salerno, and P. Curatolo, *Neurologic aspects of adenylosuccinate lyase deficiency*. J Child Neurol, 2001.16(5): p. 301-8.
Gitiaux, C., et al., *Misleading behavioural phenotype with adenylosuccinate lyase deficiency*.Eur J Hum Genet, 2009.17(1): p. 133-6.
Mierzewska, H., et al., *Severe encephalopathy with brain atrophy and hypomyelination due to adenylosuccinate lyase deficiency—MRI, clinical, biochemical and neuropathological findings of Polish patients*. Folia Neuropathol, 2009.47(4): p. 314-20.
Eissmann, M., et al., *A functional yeast survival screen of tumor-derived cDNA libraries designed to identify anti-apoptotic mammalian oncogenes*. PLoS One, 2013.8(5): p. e64873.
Goswami, M.T., et al., *Role and regulation of coordinately expressed de novo purine biosynthetic enzymes PPAT and PAICS in lung cancer*. Oncotarget, 2015.6(27): p. 23445-61.
Chakravarthi, B.V., et al., *Expression and Role of PAICS, a De Novo Purine Biosynthetic Gene in Prostate Cancer*. Prostate, 2017.77(1): p. 10-21.

Keller, K.E., I.S. Tan, and Y.S. Lee, *SAICAR stimulates pyruvate kinase isoform M2 and promotes cancer cell survival in glucose-limited conditions*. Science, 2012.338(6110): p. 1069-72.
Keller, K.E., et al., *SAICAR induces protein kinase activity of PKM2 that is necessary for sustained proliferative signaling of cancer cells*. Mol Cell, 2014.53(5): p. 700-9.
Spiegel, E.K., Colman, R.F., and Patterson, D. (2006). *Adenylosuccinate lyase deficiency*. Mol Genet Metab 89, 19-31.
Clamadieu, C., Cottin, X., Rousselle, C., and Claris, O. (2008). *Adenylosuccinate lyase deficiency: an unusual cause of neonatal seizure*. Arch Pediatr 15, 135-138.
Castro, M., Perez-Cerda, C., Merinero, B., Garcia, M.J., Bernar, J., Gil Nagel, A., Torres, J., Bermudez, M., Garavito, P., Marie, S., et al. (2002). *Screening for adenylosuccinate lyase deficiency: clinical, biochemical and molecular findings in four patients*. Neuropediatrics 33, 186-189.
Criss W E. A Review of Polyamines and Cancer [J]. *Turkish Journal of Medical Sciences*, 2003, 33(4): 195-205.
Gerner EW, Meyskens FL Jr. Polyamines and cancer: old molecules, new understanding.[J]. *Nat Rev Cancer*. 2004, 4(10): 781-792.
Rial NS, Meyskens FL, Gerner EW. Polyamines as mediators of APC-dependent intestinal carcinogenesis and cancer chemoprevention [J]. *Essays in biochemistry*, 2009, 46(Suppl.1): 111.
Amendola R, Cervelli M, Fratini E, et al. Spermine metabolism and anticancer therapy[J]. *Current cancer drug targets*, 2009, 9(2): 118-130.
Mandal S, Mandal A, Johansson H E, et al. Depletion of cellular polyamines, spermidine and spermine, causes a total arrest in translation and growth in mammalian cells [J]. *Proceedings of the National Academy of Sciences of the United States of America*, 2013, 110(6): 2169-74.
*Pharmaceutical Salts: Properties, Selection and Use*, P Heinrich Stahl (Editor), Camille G. Wermuth (Editor), ISBN: 3-90639-026-8, Hardcover, 388 pages, Aug. 2002.
Zhang Jun, "Study on Mechanism of Apoptosis Induced by Spermidine in Human Cervical Cancer Hela Cells", China Master's Theses Full-text Database, Apr. 1, 2013, body text, p. 28, chapter 5, Conclusion.
Tian Yihong, "Study on the Relationship between Autophagy and Viability Decrease of Hela Cells Induced by Spermidine", China Master's Theses Full-text Database, Apr. 1, 2013, body text, p. 31, chapter 5, Conclusions.
Zhang Feng et al., "Research Progress on Effect of Extrinsic Spermidine on Resistance of Organism", Chemistry & Bioengineering, 32(7), Jul. 25, 2015, pp. 1-4 and 21.
AU Office Action in Australian Appln. No. 2018253671, dated Jun. 18, 2020, 4 pages.
AU Office Action in Australian Appln. No. 2018253671, dated Mar. 17, 2020, 5 pages.
Hmdb.ca [online], "Showing metabocard for SAICAR (HMDB0000797)," updated Oct. 9, 2020, [Retrieved on Jun. 17, 2021], retrieved from: URL<https://hmdb.ca/metabolites/HMDB0000797>, 10 pages.
Igarashi, Pharmacia, 1995, 31(4):373-377 (with English Abstract only).
JP Notice of Allowance in Japanese Appln. No. 2019516529, dated May 20, 2021, 5 pages (with English Translation).
JP Notice of Allowance in Japanese Appln. No. 2019551698, dated Nov. 20, 2020, 5 pages (with English Translation).
JP Office Action in Japanese Appln. No. 2019516529, dated Mar. 10, 2021, 6 pages (with English Translation).
JP Office Action in Japanese Appln. No. 2019516529, dated Sep. 7, 2020, 9 pages (with English Translation).
JP Office Action in Japanese Appln. No. 2019551698, dated Jul. 17, 2020, 10 pages (with English Translation).
KR Office Action in Korean Appln. No. 20197028417, dated Dec. 17, 2020, 15 pages (with English Translation).
Manjunath et al., "Catalytic pathway, substrate binding and stability in SAICAR synthetase: A structure and molecular dynamics study," Journal of Structural Biology, Jun. 2015, 191:22-31, http://dx.doi.org/10.1016/j.jsb.2015.06.006, 10 pages.
Marinaki et al., "Adenylosuccinate Lyase Deficiency—First British Case," Nucleosides Nucleotides & Nucleic Acids, Oct. 2004, 23(8-

(56) References Cited

OTHER PUBLICATIONS

9):1231-1233, copy downloaded by University of Saskatchewan Library, doi: 10.1081/NCN-200027494.

Ostanin et al., "Isolation and properties of phosphoribosyl succinocarboxamideaminoimidazole synthetase from the yeast *Saccharomyces cerevisiae*," Biokhimiia (Moscow, Russia), 1989, 54(8):1265-1273 (with English Abstract).

PCT International Preliminary Report on Patentability in International Appln. No. PCT/CN2017/101062, dated Apr. 2, 2019, 21 pages (with English Translation).

PCT International Preliminary Report on Patentability in International Appln. No. PCT/CN2017/101064, dated Apr. 2, 2019, 10 pages (with English Translation).

PCT International Preliminary Report on Patentability in International Appln. No. PCT/CN2017/101066, dated Apr. 2, 2019, 14 pages (with English Translation).

PCT International Preliminary Report on Patentability in International Appln. No. PCT/CN2017/103405, dated Apr. 2, 2019, 14 pages (with English Translation).

PCT International Preliminary Report on Patentability in International Appln. No. PCT/CN2018/075427, dated Oct. 22, 2019, 11 pages (with English Translation).

PCT International Preliminary Report on Patentability in International Appln. No. PCT/CN2018/078597, dated Oct. 22, 2019, 16 pages (with English Translation).

PCT International Search Report and Written Opinion in International Appln. No. PCT/CN2017/101062, dated Dec. 8, 2017, 29 pages (with English Translation).

PCT International Search Report and Written Opinion in International Appln. No. PCT/CN2017/101064, dated Dec. 11, 2017, 16 pages (with English Translation).

PCT International Search Report and Written Opinion in International Appln. No. PCT/CN2017/101066, dated Dec. 29, 2017, 19 pages (with English Translation).

PCT International Search Report and Written Opinion in International Appln. No. PCT/CN2017/103405, dated Jan. 4, 2018, 22 pages (with English Translation).

PCT International Search Report and Written Opinion in International Appln. No. PCT/CN2018/075427, dated Apr. 12, 2018, 17 pages (with English Translation).

PCT International Search Report and Written Opinion in International Appln. No. PCT/CN2018/078597, dated Apr. 27, 2018, 24 pages (with English Translation).

Soda et al., "Increased Polyamine Intake Inhibits Age-Associated Alteration in Global DNA Methylation and 1,2-Dimethylhydrazine-Induced Tumorigenesis," Plos One, 2013, 8(5):e64357, 7 pages.

Agarwal et al., "PAICS, a De Novo Purine Biosynthetic Enzyme, Is Overexpressed in Pancreatic Cancer and Is Involved in Its Progression," Transl Oncol, 2020, 13(7):100776, 10 pages.

Agarwal et al., "PAICS, a Purine Nucleotide Metabolic Enzyme, Is Involved in Tumor Growth and the Metastasis of Colorectal Cancer," Cancers (Basel), 2020, 12(4):772, 26 pages.

Alaoui-Ismaili et al., "Design of second generation therapeutic recombinant bone morphogenetic proteins," Cytokine Growth Factor Rev., 2009, 20:501-507.

AU Office action in Australian Appln. No. 2018253689, dated Mar. 20, 2020, 4 pages.

Balabhadrapatruni et al., "Expression and Role of PAICS, a De Novo Purine Biosynthetic Gene in Prostate Cancer," The Prostate, 2017, 77:10-21.

Baresova et al., "Mutations of ATIC and ADSL affect purinosome assembly in cultured skin fibroblasts from patients with AICA-ribosiduria and ADSL deficiency," Hum. Mol. Genet., 2012, 21(7):1534-1543.

Biovaria.org, [Online], "Small molecule PAICS inhibitors for metastatic breast cancer," May 2016, retrieved on Aug. 26, 2020, retrieved from URL<https://www.biovaria.org/uploads/tx_biotechnologies/C1_PAICS_Slides_Biovaria_V2.pdf>, 9 pages.

Bullinger et al., "Metabolic signature of breast cancer cell line MCF-7: profiling of modified nucleosides via LC-IT MS coupling," BMC Biochem., 2007, 8:25, 14 pages.

Burgess et al., "Possible dissociation of the heparin-binding and mitogenic activities of heparin-binding (acidic fibroblast) growth factor-1 from its receptor-binding activities by site-directed mutagenesis of a single lysine residue," J of Cell Bio, 1990, 111(5 pt. 1):2129-2138.

Casey et al., "Inhibition of Adenylosuccinate Lyase by L-alanosyl-5-aminoimidazole- 4-carboxylic Acid Ribonucleotide (Alanosyl-AICOR)." Biochemical Pharmacology, 1987, 36(5):705-709.

Casey et al., "Metabolism of threo-,8-Fluoroaspartate by H4 Cells," J. Biol. Chem., 1986, 261(29):13637-13642.

Chadwick et al., "Design, synthesis and antimalarial/anticancer evaluation of spermidine linked artemisinin conjugates designed to exploit polyamine transporters in Plasmodium falciparum and HL-60 cancer cell lines," Biorganic Med. Chem., 2010, 18:2586-2597.

Chakravarthi et al., "A Role for De Novo Purine Metabolic Enzyme PAICS in Bladder Cancer Progression," Neoplasia, 2018, 20(9):894-904.

Chen et al., "The Non-Essentiality of Essential Genes in Yeast Provides Therapeutic Insights into a Human Disease." Genome Res, 2016, 26(10):1355-1362.

Chipperfiel et al., "Effects on the Activity of the Enzyme Phosphoribosyl-Aminoimidazole Carboxylase, 5'-Phosphate," Nucleosides and Nucleotides, 1988, 7(5-6):571-576.

Devens et al., "Polyamine Depletion Therapy in Prostate Cancer," Prostate Cancer & Prostat. Diseases, 2000, 3:275-279.

Drugbank.com, [Online], "Spermidine, Accession No. DB03566," Dec. 2019, retrieved on Dec. 12. 2019, retrieved from URL<www.drugbank.ca/drugs/DB03566>, 11 pages.

Ebi.ac.uk. [Online], "Spermidine (CHEBI:16610), DB03566," Jan. 2019, retrieved on Dec. 12, 2019, retrieved from URL<www.ebi.ac.uk/chebi/fr/searchld.do;266979CDB4296779F98B8B8B21B2278B?printerFriendlyView=true&locale=null&chebild=16610&viewTermlineage=null&structureView=&>. 7 pages.

EP Office Action in European Appln. No. 17854846.7-1109, dated May 11, 2020, 9 pages.

Guo et al., "Protein tolerance to random amino acid change," PNAS, 2004, 101(25):9205-9210.

Hargis et al., "Identification and Characterization of Noncovalent Interactions That Drive Binding and Specificity in DD-Peptidases and β-Lactamases." J Chem Theory Comput., 2014, 10(2):855-864.

Jaeken et al., "An infantile autistic syndrome characterized by the presence of succinvlpurines in body fluids," Lancet, 8411:1058-1061.

JP Office Action in Japanese Appln. No. 2019516529, dated Jan. 30, 2020, 13 pages (with English Translation).

JP Office Action in Japanese Appln. No. 2019516529, dated May 20, 2020, 13 pages (with English Translation).

Jurecka et al., "Adenylosuccinate lyase deficiency," J. Inherit. Metab. Dis., 2015, 38:231-242.

Jurecka et al., "Clinical, biochemical and molecular findings in seven Polish patients with adenylosuccinatelyase deficiency," Mol Genet Metab, 2008, 94:435-442.

Kobayashi et al., "Abstract 3415: PAICS is the prognostic marker in colorectal cancer patients with stage III," Clin Res. 2015, 4 pages.

Le Bot et al., "SAICAR drives cancer cell survival," Nat. Cell Biol., 2013, 15:16, 1 page.

Li et al., "Octameric Structure of the Human Bifunctional Enzyme PAICS in Purine Biosynthesis," J. Mol. Biol., 2007, 366(5):1603-1614.

Madeo et al.,"Spermidine in Health and Disease," Science, 2018, 359:eaan2788, 11 pages.

Mackenzie et al., "Synthesis of analogues of 5-aminoimidazole ribonucleotides and their effects as inhibitors and substrates of the enzymes, phosphoribosylaminoimidazole carboxylase and phosphoribosylaminoimidazolesuccinocarboxamide synthetase involved in the biosynthesis of purine nucleotides de novo," Journal of the Chemical Society, Chemical Communications, 1976, 12:453-455.

Meng et al., "Knockdown of PAICS Inhibits Malignant Proliferation of Human Breast Cancer Cell Lines," Biol Res., 2018, 51(1):24, 9 pages.

(56) References Cited

OTHER PUBLICATIONS

Meng, "DNA Mutation/Methylation Screening Method For Colon Cancer Screening," PhD Dissertation, Cleveland University, Nov. 2010, 157 pages.
Murray-Stewart et al., "Targeting Polyamine Metabolism for Cancer Therapy and Prevention," Biochem. J., 2016, 473(19):2937-2953.
Nelson et al., "Mechanism of Action of *Escherichia coli* Phosphoribosylaminoimidazolesuccinocarboxamide Synthetase†," Biochemistry, 2005, 44(2):766-774.
Noro et al., "Spermidine Ameliorates Neurodegeneration in a Mouse Model of Normal Tension Glaucoma," IOVS, 2015, 56:5012-5019.
Nowotarski et al., "Polyamines and Cancer: Implications for Chemotherapy and Chemoprevention," Expert. Rev. Mol. Med., 2013, 15:e3, 21 pages.
Pawson et al., "Assembly of Cell Regulatory Systems Through Protein Interaction Domains," 2003, Science 300:445-452.
PCT International Preliminary Report on Patentability in International Appln. No. PCT/CN2017/103408, dated Apr. 2, 2019, 22 pages (with English Translation).
PCT International Preliminary Report on Patentability in International Appln. No. PCT/CN2018/078723, dated Oct. 22, 2019, 12 pages (with English Translation).
PCT International Search Report and Written Opinion in International Appln. No. PCT/CN2017/103408, dated Dec. 5, 2017, 30 pages (with English Translation).
PCT International Search Report and Written Opinion in International Appln. No. PCT/CN2018/078723, dated May 21, 2018, 16 pages (with English Translation).
Pegg, "Critical Review: The Function of Spermine," IUBMB Life, 2014, 66:8-18.
Pietrocola et al., "Caloric Restriction Mimetics Enhance Anticancer Immunosurveillance," Cancer Cell, 2016, 30:147-160.
Pietrocola et al., "Spermidine reduces cancer-related mortality in humans," Autophagy, 2019, 15(2):362-365.
Porter et al., "Relative abilities of bis(ethyl) derivatives of putrescine, spermidine, and spermine to regulate polyamine biosynthesis and inhibit L1210 leukemia cell growth," Cancer Res., 1987, 47(11):2821-5.
Porter et al.,"Biological properties of N4- and N1,N8-spermidine derivatives in cultured L1210 leukemia cells," Can. Res., 1985, 45(5):2050-2057.
RareDiseases.info.nih.gov, [Online], "Adenylosuccinase Deficiency," Sep. 2011, retrieved on Dec. 13, 2019, retrieved from URL<rarediseases.info.nih.gov/diseases/550/adenylosuccinase-deficiency>, 38 pages.
Scott et al., "Reconstitution of apo-porphobilinogen deaminase: Structural changes induced by cofactor binding." FEES Letters, 1989, 242(2):319-324.
Soda, "The mechanisms by which polyamines accelerate tumor spread," J. Exp. Clin. Cancer Res., 2011, 30:95, 9 pages.
Stark et al., "Synthesis and Evaluation of Novel Spermidine Derivatives as Targeted Cancer Chemotherapeutic Agents," J. Med. Chem., 1992, 35:4264-4269.
Tsoi et al., "Urinary Polyamines: A Pilot Study on Their Roles as Prostate Cancer Detection Biomakers," PLoS One, 2016, 11:e0162217, 13 pages.
Van den Bergh et al., "Residual adenylosuccinase activities in fibroblasts of adenylosuccinase-deficient children: parallel deficiency with adenylosuccinate and succinl-AICAR in profoundly retarded patients and non-parallel deficiency in a mildly retarded girl," J. Inherit. Metab. Dis., 1993, 16(2):415-424.
Webb et al., "A Series of Related Nucleotide Analogues that Aids Optimization of Fluorescence Signals in Probing the Mechanism of P-Loop ATPases, Such as Actomyosin †," Biochemistry, 2004, 42(45):14463-14471.
WO2014067038—English translated version, published May 8, 2014.
Zhang, "Study on the Apoptosis of Hela Cells Induced by Spermidine," Master Thesis, Apr. 2013, 44 pages, English Abstract.
Zhou et al., "Roles of highly expressed PAICS in lung adenocarcinoma," Gene, 2019, 692:1-8.
Zikanova et al., "Preparation of 5-amino-4-imidazole-N-succinocarboxamide ribotide, 5-amino-4-imidazole-N-succinocarboxamide riboside and succinyladenosine, compounds usable in diagnosis and research of adenylosuccinate lyase deficiency," Journal of Inherited Metabolic Disease, 2005, 28(4):493-499.
CA Office Action in Canadian Appln. No. 3057206, dated Mar. 31, 2021, 4 pages.
CA Office Action in Canadian Appln. No. 3057206, dated Oct. 23, 2020, 6 pages.
CA Office Action in Canadian Appln. No. 3064486, dated Mar. 12, 2021, 4 pages.
EP Office Action in European Appln. No. 18787222.1, dated Mar. 2, 2021, 6 pages.
EP Search Report in European Appln. No. 18787222.1, dated Sep. 18, 2020, 9 pages.
EP Search Report in European Appln. No. 18788316.0, dated Dec. 15, 2020, 8 pages.
KR Office Action in Korean Appln. No. 20197028417, dated Jun. 28, 2021, 10 pages (with English Translation).
KR Office Action in Korean Appln. No. 20197028417, dated Aug. 30, 2021, 7 pages (with English Translation).
Kuo et al., "A systems analysis of the chemosensitivity of breast cancer cells to the polyamine analogue PG-11047," BMC Medicine, BioMed Central, Dec. 2009, 7:77, doi:10.1186/1741-7015-7-77.
ATCC [Online], "Product Sheet: L-1210—CCL-219™," Updated May 19, 2021, [Retrieved on Jan. 18, 2022], retrieved from: URL<https://www.atcc.org/products/ccl-219>, 6 pages.
Bachrach et al., "Polyamines: New Cues in Cellular Signal Transduction," News Physiol. Sci., Jun. 2001, 16:106-9.
EP Office Action in European Appln. No. 17854846.7, dated Jul. 6, 2022, 4 pages.
Gaude et al., "Tissue-specific and convergent metabolic transformation of cancer correlates with metastatic potential and patient survival," Nature Communications, 2016, 7:13041.
John Hopkins Medicine [Online], "Invasive Mammary Carcinoma (IMC)," available on or before Feb. 3, 2022, [Retrieved on Jan. 18, 2022], retrieved from: URL<https://www.hopkinsmedicine.org/breast_center/breast_cancers_other_conditions/invasive_mammary_carcinoma.html>, 1 page.
Office Action in Chinese Appln. No. 201880019008.9, dated Mar. 9, 2022, 11 pages (with English translation).
Office Action in Chinese Appln. No. 201880031224.5, dated May 7, 2022, 11 pages (with English Translation).
Tian, "Study on the Relationship between Autophagy and Viability Decrease of Hela Cells Induced by Spermidine," Abstract, China Master's Theses Full-text Database, Apr. 2013, 4 pages (with Machine Abstract).

\* cited by examiner

Control (no spermidine)    Experimental group (with spermidine)
(MYC is significantly inhibited)

Fig. 5

APPLICATIONS OF SPERMIDINE AND ITS DERIVATIVES

CROSS-REFERENCE TO RELATED APPLICATIONS

This application is based upon and claims priority to Chinese Patent Application No. 201710262440.8, filed on Apr. 20, 2017, the entire contents of which are incorporated herein by reference.

TECHNICAL FIELD

The present disclosure relates to novel use of a compound, and particularly to the use of spermidine and the derivatives thereof.

BACKGROUND ART

One important hallmark of cancer cells is metabolic reprogramming, including increased glucose uptake and oxygen-independent lactate fermentation, which is also known as Warburg effect [1, 2]. Such reprogramming is necessary for the growth and survival of tumors, especially under pressure conditions such as ambient hypoxia. However, it is still unclear for the important molecular mechanism, as well as the action mode for the correlation of the metabolic reprogramming of tumor cells with the rapid proliferation, differentiation, migration and the like of tumors.

Pyruvate kinase isoform M2 (PKM2), as one important enzyme in metabolic process, is highly expressed in most tumor cells which undergo rapid proliferation, and has great influence on the metabolism and growth of tumor cells [3, 4]. In addition, various pharmacological agents against PKM2 enzyme activity can affect the growth and proliferation of cells [5, 6]. It also suggests that altering tumor metabolism by targeting the enzyme activity of PKM2 would become a new approach for tumor therapy [7].

Purine metabolism is a ubiquitous and important biological metabolism in organisms. Its products, AMP and GMP, provide not only starting materials for the biosynthesis of DNA and RNA in the organisms, but also purine bases which are necessary for the in vivo synthesis of many key coenzymes (e.g. NAD, NADP, FAD and CoA), signal molecules (e.g. cAMP) and an important energy molecule ATP. It is thus evident that the purine metabolism is at the core position of the whole metabolic network. Purine synthesis comprises two synthetic pathways, i.e. de novo purine synthesis and salvage pathway.

In the adenine de novo synthesis pathway, adenylosuccinate lyase (hereinafter referred to as ADSL enzyme) mainly participates in the catalyzing and cleaving of SAICAR to form AICAR and in the generation of AMP from S-AMP [Spiegel, E. K., Colman, R. F., and Patterson, D. (2006). *Adenylosuccinate lyase deficiency*, Mol Genet Metab 89, 19-31. Clamadieu, C., Cottin, X., Rousselle, C., and Claris, O. (2008). *Adenylosuccinate lyase deficiency: an unusual cause of neonatal seizure*. Arch Pediatr 15, 135-138. Castro, M., Perez-Cerda, C., Merinero, B., Garcia, M. J., Bernar, J., Gil Nagel, A., Torres, J., Bermudez, M., Garavito, P., Marie, S., et al. (2002). *Screening for adenylosuccinate lyase deficiency: clinical, biochemical and molecular findings in four patients*. Neuropediatrics 33, 186-189].

In human bodies, abnormal metabolic enzyme in the adenine de novo synthesis pathway often leads to the accumulation of deleterious intermediate metabolite succinyl-5-aminoimidazole-4-carboxamide-1-ribose-50-phosphate (SAICAR), which has clinical symptoms such as autism, epilepsy, hypotonia, and dysplasia [8-10]. SAICAR synthase is encoded by gene PAICS (phosphoribosylaminoimidazole succinocarboxamide synthetase/phosphoribosylaminoimidazole carboxylase), and is responsible for the synthesis of SAICAR in vivo. Related studies have reported that PAICS is highly expressed in acute lymphocytic leukemia, lung cancer, glioma, prostate cancer and colorectal cancer, and can be used as a prognostic marker for stage III colorectal cancer [11-13]. Recent studies have found that SAICAR can be highly accumulated under glucose-limited conditions, and then alter energy level, sugar uptake, and generation of lactic acid in tumor cells. However, these phenomena are not found in adult epidermal cells and lung fibroblasts [14, 15]. SAICAR can induce the enzymatic activity of PKM2 and promote the survival of tumor cells [14]. Moreover, the binding of SAICAR-PKM2 can induce the phosphorylation of Erk1/2, and SAICAR in high concentration can also induce the up-regulated expression of oncogene myc [15]. The accumulated SAICAR due to abnormal adenine de novo synthesis pathway promotes the proliferation and survival of tumor cells.

Phosphoribosylaminoimidazole succinocarboxamidesynthetase/phosphoribosylaminoimidazole carboxylase, i.e. PAICS, is an important bifunctional enzyme in the purine de novo synthesis pathway, and has the functions of SAICAR synthetase (4-(N-succinylcarboxamide)-5-aminoimidazole ribonucleotide synthetase, SAICARs) and AIR carboxylase (5-aminoimidazole ribonucleotide carboxylase, AIRc). PAICS catalyzes the sixth and seventh steps of the purine de novo synthesis, in which one key reaction process is shown as follows:

Therefore, tumors having abnormally high expression of PAICS are often accompanied by the accumulation of deleterious metabolite SAICAR. Researches on inhibiting the expression of PAICS or its enzymatic activity will become new means for tumor therapy. It is very important to develop or screen out compounds that can effectively inhibit the activity of PAICS.

Spermidine is an important polyamine in vivo, and plays an important role in life activities of living organisms and involves in many processes such as cell migration, cell growth and tumorigenesis. Spermidine also plays an important role in the maintenance of the structure stability of DNA, RNA and cell membranes, in the synthesis of proteins, and in the regulation of ion channels. The catabolism of spermidine may produce many metabolites such as free radicals, and may influence cell vitality. Spermidine is often overexpressed in tumor tissues, as disclosed by authoritative papers such as Criss W E. A Review of Polyamines and Cancer [J]. *Turkish Journal of Medical Sciences*, 2003, 33(4): 195-205; Gerner E W, Meyskens F L Jr. Polyamines and cancer: old molecules, new understanding. [J]. *Nat Rev Cancer*, 2004, 4(10): 781-792; Rial N S, Meyskens F L, Gerner E W. Polyamines as mediators of APC-dependent intestinal carcinogenesis and cancer chemoprevention [J]. *Essays in biochemistry*, 2009, 46(Suppl.1): 111; Amendola R, Cervelli M, Fratini E, et al. Spermine metabolism and anticancer therapy[J]. *Current cancer drug targets*, 2009, 9(2): 118-130; Mandal S, Mandal A, Johansson H E, et al. Depletion of cellular polyamines, spermidine and spermine, causes a total arrest in translation and growth in mammalian cells [J]. *Proceedings of the National Academy of Sciences of the United States of America*, 2013, 110(6): 2169-74. It has long been known that spermidine can promote the development of tumor cells and is a tumor promoter. Therefore, it is conductive to cancer-fighting by reducing the supply of spermidine.

REFERENCES

1. Hanahan, D. and R. A. Weinberg, *Hallmarks of cancer: the next generation*. Cell, 2011. 144(5): p. 646-74.

2. Hsu, P. P. and D. M. Sabatini, *Cancer cell metabolism: Warburg and beyond*. Cell, 2008. 134(5): p. 703-7.

3. Christofk, H. R., et al., *The M2 splice isoform of pyruvate kinase is important for cancer metabolism and tumour growth*. Nature, 2008. 452(7184): p. 230-3.

4. Wolf, A., et al., *Hexokinase 2 is a key mediator of aerobic glycolysis and promotes tumor growth in human glioblastoma multiforme*. J Exp Med, 2011. 208(2): p. 313-26.

5. Chen, J., et al., *Shikonin and its analogs inhibit cancer cell glycolysis by targeting tumor pyruvate kinase-M2*. Oncogene, 2011. 30(42): p. 4297-306.

6. Anastasiou, D., et al., *Pyruvate kinase M2 activators promote tetramer formation and suppress tumorigenesis*. Nat Chem Biol, 2012. 8(10): p. 839-47.

7. Vander Heiden, M. G., *Exploiting tumor metabolisms challenges for clinical translation*. J Clin Invest, 2013. 123(9): p. 3648-51.

8. Ciardo, F., C. Salerno, and P. Curatolo, *Neurologic aspects of adenylosuccinate lyase deficiency*. J Child Neurol, 2001. 16(5): p. 301-8.

9. Gitiaux, C., et al., *Misleading behavioural phenotype with adenylosuccinate lyase deficiency*. Eur J Hum Genet, 2009. 17(1): p. 133-6.

10. Mierzewska, H., et al., *Severe encephalopathy with brain atrophy and hypomyelination due to adenylosuccinate lyase deficiency—MRI, clinical, biochemical and neuropathological findings of Polish patients*. Folia Neuropathol, 2009. 47(4): p. 314-20.

11. Eissmann, M., et al., *A functional yeast survival screen of tumor-derived cDNA libraries designed to identify antiapoptotic mammalian oncogenes*. PLoS One, 2013. 8(5): p. e64873.

12. Goswami, M. T., et al., *Role and regulation of coordinately expressed de novo purine biosynthetic enzymes PPAT and PAICS in lung cancer*. Oncotarget, 2015. 6(27): p. 23445-61.

13. Chakravarthi, B. V., et al., *Expression and Role of PAICS, a De Novo Purine Biosynthetic Gene in Prostate Cancer*. Prostate, 2017. 77(1): p. 10-21.

14. Keller, K. E., I. S. Tan, and Y. S. Lee, *SAICAR stimulates pyruvate kinase isoform M2 and promotes cancer cell survival in glucose-limited conditions*. Science, 2012. 338(6110): p. 1069-72.

15. Keller, K. E., et al., *SAICAR induces protein kinase activity of PKM2 that is necessary for sustained proliferative signaling of cancer cells*. Mol Cell, 2014. 53(5): p. 700-9.

SUMMARY OF THE INVENTION

An objective of the present disclosure is to provide use of a class of compounds interfering with the activity of SAICAR synthase.

The inventors, on the basis of existing data relating to protein and small-molecule structures, performed calculation and analysis using software, and found that a compound with DrugBank ID DB03566 (general name: spermidine) can effectively interfere with the activity of PAICS and thus reduce SAICAR synthesis, thereby achieving the goal of beating or improving tumors.

The tumor may be one having any property selected from Warburg effect, high expression of oncogene myc, high expression of PAICS, being associated with Erk1/2, and high expression of PKM2 gene. In particular, the tumor may be selected from acute lymphocytic leukemia, lung cancer, glioma, prostate cancer, colorectal cancer, gastric cancer, liver cancer, esophageal cancer, colon cancer, malignant lymphoma, cervical cancer, nasopharyngeal cancer, breast cancer, skin cancer or bladder cancer, and especially may be selected from acute lymphocytic leukemia, lung cancer, glioma, prostate cancer or colorectal cancer which have the high expression of PAICS.

As used herein, the term "high expression" has the meaning well known in the art, and refers to the expression which is significantly increased as compared to that of a normal tissue.

The pharmaceutically acceptable derivatives of the above compound may have the same parent core structure as the compound per se, and can produce molecules having the same or similar activity as the original compound through in vivo reactions such as hydrolysis and the like. Thus, the pharmaceutically acceptable derivatives can have the same or similar therapeutic effect as that of the original compound.

The pharmaceutically acceptable derivatives of the compound may particularly refer to simple derivatives thereof, especially to one of lower ester, lower ether, lower alkyl substituent, a medicinal salt and lower amide thereof. That is, the pharmaceutically acceptable derivatives may be derivatives obtained by a condensation reaction between the parent compound with carboxylic acid, alcohol or amine having 1 to 6, preferably 2 to 6, and 2 to 4 carbon atom(s).

The pharmaceutically acceptable medicinal salt of the compound can be synthesized from the parent compound by a conventional chemical method, such as the method described in *Pharmaceutical Salts: Properties, Selection and Use,* P Heinrich Stahl (Editor), Camille G. Wermuth (Editor), ISBN: 3-90639-026-8, Hardcover, 388 pages, August 2002. in general, such salts can be prepared by reacting free alkali of the compound with an acid in water, an organic solvent or a mixed solution of both, generally in a non-aqueous media such as diethyl ether, ethyl acetate, ethanol, isopropanol or acetonitrile.

The acid addition salt can be prepared using various acids such as inorganic and organic acids. The examples of the acid addition salt may include salts prepared from acids, which may be selected from a group consisting of acetic acid, 2,2-dichloroacetic acid, adipic acid, alginic acid, ascorbic acid (e.g. L-ascorbic acid), L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid (e.g. D-glucuronic acid), glutamic acid (e.g. L-glutamic acid), α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acids.

With combined utilization of at least two of the above compounds, it is expected to obtain better effect of treating and improving tumors.

BRIEF DESCRIPTION OF THE DRAWINGS

FIG. 2 shows the diagrams indicating the interaction of the crystal structures of CAIR and SAICAR synthetase, in which A: PDB access ID 2GQS; B: PDB access ID 2CNQ; and C: PDB access ID 4FE2;

FIG. 3 shows the alignment result of the protein sequences of SAICAR synthetases from different species;

DETAILED DESCRIPTION OF THE EMBODIMENTS

Figure 1:
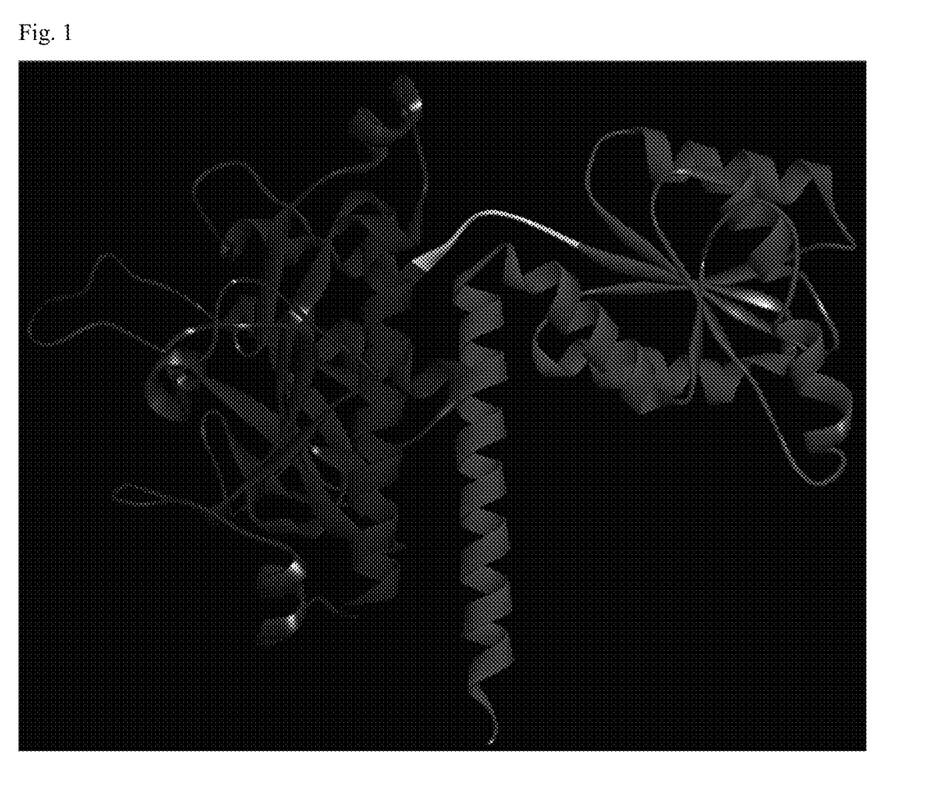
FIG. 1 shows the 3D solid ribbon structure diagram of PAICS.

There are 425 amino acid residues in the full length of the human PAICS protein sequence, in which 2-260AA is a SAICAR synthetase domain and 267-425AA is AIR carboxylase domain, these two domains are linked by a peptide chain consisting of 6 amino acid residues (KSESQC). Furthermore, GLN159-GLN183 α-helix in the SAICAR synthetase domain and ASN395-ASN424 α-helix in the AIR carboxylase domain interact with each other and are tightly bound together, as shown in FIG. 1.

SAICAR synthetase crystal structure data of different origins are collected in a protein structure database (RCSB), which includes *Saccharomyces cerevisiae* (1A48, 2CNQ, 2CNV, 2CNU, 1OBD, 1OBG), *Pyrococcushorikoshii* OT3 (3U54, 3U55), *Escherichia coli* (2GQR, 2GQS), *Methanocaldococcus jannaschii* (2YZL, 2Z02), *Streptococcus pneumonia* (4FGR, 4FE2), *Mycobacterium abscessus* ATCC 19977/DSM 44196 (3R9R), *Thermotoga maritime* (1KUT), *Clostridium perfringens* (3NUA), *Ehrlichia chaffeensis* (3KRE), *Geobacillus kaustophilus* (2YWV), as well as PAICS crystal structure data of *Homo sapiens* (2H31) and *Bombyx mori* (4JA0). Wherein, the complexes containing the structure of CAIR are 2GQS, 2CNQ and 4FE2, and the complexes containing the structure of ASP are 2CNV, 2CNU and 4FE2.

Figure 2A:
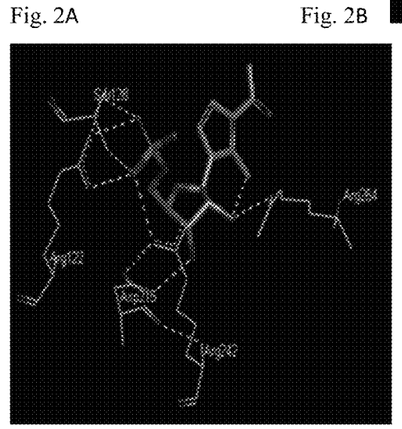
Figure 2B:
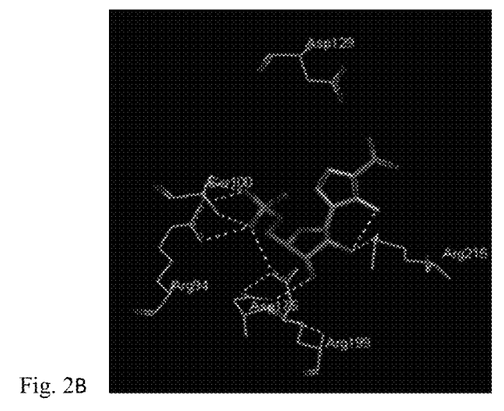
Figure 2C:
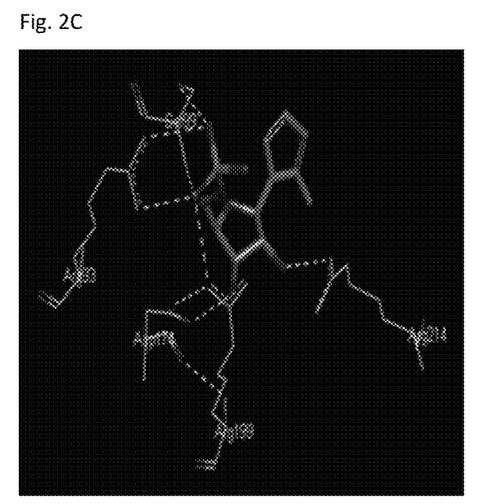

As shown in FIG. 2, the residues within CAIR 3 Å in 2CNQ comprise Arg122, Ser128, ASP215, Arg242 and Arg264; the residues within CAIR 3 Å in 2GQS comprise Arg94, Ser100, ASP129, ASP175, Arg199 and Arg215; and the residues within CAIR 3 Å in 4FE2 comprise Arg93, Ser99, ASP174, Arg 199 and Arg 214. As can be seen from the alignment results of SAICAR protein sequences from different species (FIG. 3), it is highly conservative for the sequence, which binds with CAR, of SAICAR synthetases from different species, and CAIR is primarily fixed by hydrogen bonds.

On the basis of the above results, the crystal structure conformations in SAICAR synthetases of *Saccharormyces cerevisiae* (PDB: 2CNQ) and *Escherichia coli* (PDB: 2GQS) are used as receptor structures for calculating and screening, since there is no conformation which can bind CAIR in human PAICS crystal structure, and is no catalytic conformation formed in the catalytic region, and the results obtained by calculation thereof would be unreliable. 4661 of small molecule drugs in DrugBank (http://www-.drugbank.ca/downloads #structures) are calculated and screened by using ligand fit module of Discovery studio.

The calculation results show that DB03566 (general name: Spermidine) has a Dock Score of 239.22, indicating that the compound spermidine can effectively interact with PAICS, and influence the synthesis of SAICAR. Thus, it can be expected to develop into tumor-treating medicines or health care products. Said tumor may be one having any property selected from Warburg effect, high expression of oncogene myc, high expression of PAICS, being associated with Erk1/2 and high expression of PKM2 gene. In particular, said tumor may be selected from acute lymphocytic leukemia, lung cancer, glioma, prostate cancer, colorectal cancer, gastric cancer, liver cancer, esophageal cancer, colon cancer, malignant lymphoma, cervical cancer, nasopharyngeal cancer, breast cancer, skin cancer or bladder cancer, and especially be acute lymphocytic leukemia, lung cancer, glioma, prostate cancer or colorectal cancer which has high expression of PAICS.

Experimental Result Data of the Inhibition of Spermidine on PAICS Activity

It is confirmed by further biochemical enzyme activity experiments and cell biology experiments that the compound spermidine can inhibit the accumulation of SAICAR up to 68.98%. The accumulation of toxic compound SAICAR is reduced by inhibiting the activity of PAICS.

Experimental Result Data of the Inhibition of Spermidine on Oncogene MYC

Figure 4:
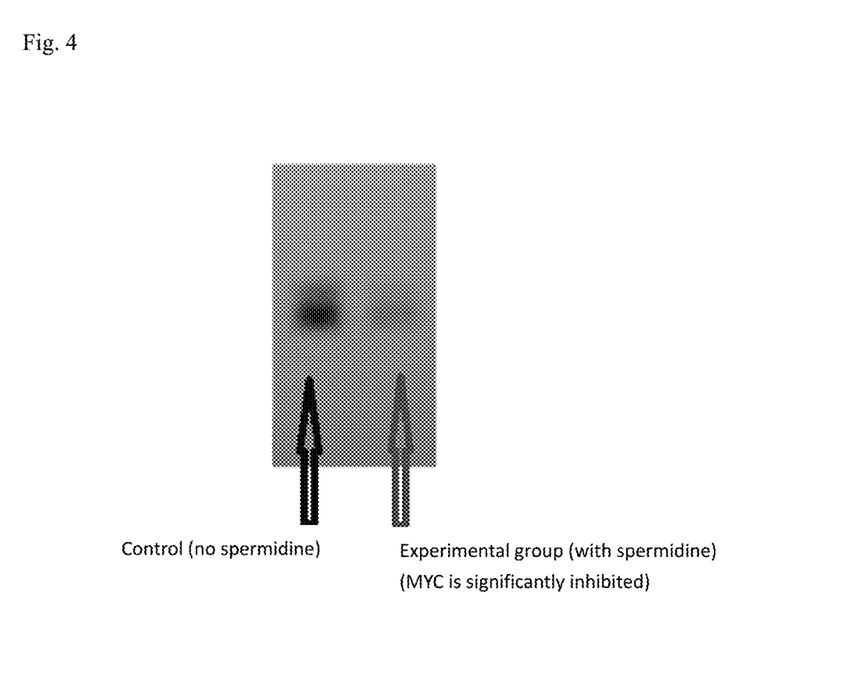
FIG. 4 shows the experimental result indicating the inhibition of spermidine on oncogene MY.

It is confirmed by further cell biology experiments and Western Blot experiments that the compound spermidine can significantly inhibit the expression of oncogene myc, such that the expression of oncogene myc is significantly down-regulated (the results of Western Blot are shown in FIG. 4).

Experimental Result Data of the Inhibition of Spermidine on Cancer Cells

Figure 5:
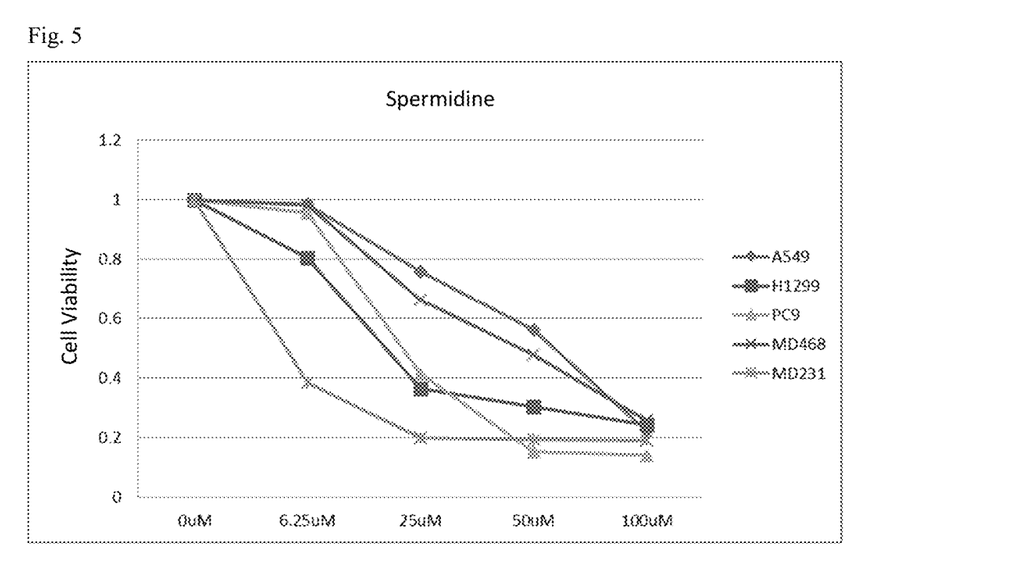
FIG. 5 shows the diagram indicating the influence of spermidine on the viability of cells.

It is confirmed by further cell biology experiments that the compound spermidine can effectively inhibit the growth of cells from a lung cancer cell strain A549, lung cancer cell strains H1299 and PC9, a breast cancer cell strain MD468, and a breast cancer cell strain MD231. FIG. 5 shows the cell viability under different concentrations of spermidine. $IC_{50}$ values after 48 hours of drug administration are shown in table below. The experimental results demonstrate that spermidine has significant anti-cancer effect.

| Cancer cells | $IC_{50}$ (μM) |
|---|---|
| A549 | 52.1 |
| H1299 | 21.1 |
| PC9 | 23.4 |
| MD468 | 46.1 |
| MD231 | 1.41 |

The above calculation data and experimental data indicate that spermidine and pharmaceutically acceptable derivatives thereof can be developed as therapeutic drugs or health care products for tumors, especially tumor having any property selected from Warburg effect, high expression of oncogene myc, high expression of PAICS, being associated with Erk1/2 and high expression of PKM2 gene. In particular, the tumor may be selected from acute lymphocytic leukemia, lung cancer, glioma, prostate cancer, colorectal cancer, gastric cancer, liver cancer, esophageal cancer, colon cancer, malignant lymphoma, cervical cancer, nasopharyngeal cancer, breast cancer, skin cancer or bladder cancer. The tumor may especially be acute lymphocytic leukemia, lung cancer, glioma, prostate cancer or colorectal cancer which has high expression of PAICS.

The pharmaceutically acceptable derivatives of compound spermidine have the same parent core structure as the compound per se, and can produce molecules having the same or similar activity as the original compound through in vivo reactions such as hydrolysis and the like. Thus, the pharmaceutically acceptable derivatives can have the same or similar therapeutic effect as that of the original compound.

The pharmaceutically acceptable derivatives of the compound particularly refers to simple derivatives thereof, especially to one of lower ester, lower ether, lower alkyl substituent, a medicinal salt and lower amide thereof. That is, the pharmaceutically acceptable derivatives may be derivatives obtained by a condensation reaction between the parent compound with carboxylic acid, alcohol or amine having 1 to 6, preferably 2 to 6, and 2 to 4 carbon atom(s).

The pharmaceutically acceptable medicinal salt of the compound can be synthesized from the parent compound by a conventional chemical method, such as the method described in *Pharmaceutical Salts: Properties, Selection and Use*, P Heinrich Stahl (Editor), Camille G. Wermuth (Editor), ISBN: 3-90639-026-8, Hardcover, 388 pages, August 2002. In general, such salts can be prepared by reacting free alkali of the compound with an acid in water, an organic solvent or a mixed solution containing the both, generally in non-aqueous media such as diethyl ether, ethyl acetate, ethanol, isopropanol or acetonitrile.

The acid addition salt can be prepared using various acids (inorganic and organic acids). The examples of the acid addition salt includes salts prepared from acids, which may be selected from a group consisting of acetic acid, 2,2-dichloroacetic acid, adipic acid, alginic acid, ascorbic acid (e.g. L-ascorbic acid), L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid (e.g. D-glucuronic acid), glutamic acid (e.g. L-glutamic acid), α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acids.

It can improve, to a certain extent, the therapeutic effect and reduce the toxic and side effect by combined usage of drugs. Preferably, two, three, four, five or more of the compounds or derivatives thereof can be used simultaneously as the active ingredients for the treatment of tumors.

What is claimed is:

1. A method for treating or relieving a tumor, comprising administering a therapeutically effect amount of spermidine or a pharmaceutically acceptable salt thereof to a patient in need thereof;
   wherein the tumor is lung cancer.

2. The method according to claim 1, wherein the method comprises administering spermidine to the patient.

3. The method according to claim 2, wherein the method comprises administering a pharmaceutically acceptable salt of spermidine to the patient.

4. The method according to claim 1, wherein the treating or relieving the tumor comprises interfering or inhibiting the activity of SAICAR synthetase.

5. The method according to claim 4, wherein the SAICAR synthetase is PAICS.

6. The method according to claim 4, wherein the tumor has at least one property selected from the group consisting of Warburg effect, high expression of oncogene myc, high expression of PAICS, being associated with Erk1/2, high expression of PKM2gene, and over-accumulation of SAICAR, SAICAr or S-Ado.

7. The method according to claim 3, wherein the pharmaceutically acceptable salt is prepared from spermidine and an acid selected from the group consisting of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, isethionic acid, (+)-L-lactic acid, (+)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl -2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acid.

8. A method for treating or relieving a tumor, comprising administering a therapeutically effect amount of spermidine or a pharmaceutically acceptable salt thereof to a patient in need thereof;
wherein the tumor is breast cancer having at least one property selected from the group consisting of Warburg effect, high expression of oncogene myc, high expression of PAICS, being associated with Erk1/2, high expression of PKM2 gene, and over-accumulation of SAICAR, SAICAr or S-Ado.

9. The method according to claim 8, wherein the method comprises administering spermidine to the patient.

10. The method according to claim 8, wherein the method comprises administering a pharmaceutically acceptable salt of spermidine to the patient.

11. The method according to claim 8, wherein the pharmaceutically acceptable salt is prepared from spermidine and an acid selected from the group consisting of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, isethionic acid, (+)-L-lactic acid, (+)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acid.

12. The method according to claim 8, wherein the treating or relieving the tumor comprises interfering or inhibiting the activity of SAICAR synthetase.

13. The method according to claim 12, wherein the SAICAR synthetase is PAICS.

14. The method according to claim 1, wherein the tumor has high expression of PAICS or over-accumulation of SAICAR.

15. A method for treating or relieving a tumor, comprising administering a therapeutically effect amount of spermidine or a pharmaceutically acceptable salt thereof to a patient in need thereof;
wherein the tumor is breast cancer having high expression of PAICS or over-accumulation of SAICAR.

16. The method according to claim 15, wherein the method comprises administering spermidine to the patient.

17. The method according to claim 15, wherein the method comprises administering a pharmaceutically acceptable salt of spermidine to the patient.

18. The method according to claim 17, wherein the pharmaceutically acceptable salt is prepared from spermidine and an acid selected from the group consisting of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, isethionic acid, (+)-L-lactic acid, (+)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acid.

19. The method according to claim 15, wherein the treating or relieving the tumor comprises interfering or inhibiting the activity of SAICAR synthetase.

20. The method according to claim 19, wherein the SAICAR synthetase is PAICS.

* * * * *